(12) United States Patent
Muster et al.

(10) Patent No.: US 8,778,357 B2
(45) Date of Patent: Jul. 15, 2014

(54) METHOD FOR GENERATION OF RNA VIRUS

(75) Inventors: Thomas Muster, Vienna (AT); Andrej Egorov, Vienna (AT); Markus Wolschek, Vienna (AT)

(73) Assignee: Baxter Healthcare SA, Glattpark (Opfikon) (CH)

( * ) Notice: Subject to any disclaimer, the term of this patent is extended or adjusted under 35 U.S.C. 154(b) by 861 days.

(21) Appl. No.: 12/630,655

(22) Filed: Dec. 3, 2009

(65) Prior Publication Data

US 2010/0184191 A1 Jul. 22, 2010

Related U.S. Application Data

(60) Provisional application No. 61/119,618, filed on Dec. 3, 2008.

(30) Foreign Application Priority Data

Mar. 19, 2009 (EP) .................................... 09155594

(51) Int. Cl.
*C12N 7/00* (2006.01)
*C07K 7/06* (2006.01)
*C07H 21/00* (2006.01)

(52) U.S. Cl.
USPC ........................ 424/235.1; 530/327; 536/22.1

(58) Field of Classification Search
None
See application file for complete search history.

(56) References Cited

U.S. PATENT DOCUMENTS

| 6,146,873 A | * | 11/2000 | Kistner et al. | ............. | 435/235.1 |
| 2007/0031941 A1 | * | 2/2007 | Duke et al. | ................... | 435/91.1 |
| 2007/0253978 A1 | * | 11/2007 | Niman | ....................... | 424/206.1 |

FOREIGN PATENT DOCUMENTS

| WO | 99/64068 | 12/1999 |
| WO | 99/64571 | 12/1999 |
| WO | 00/56914 | 9/2000 |
| WO | 00/60050 | 10/2000 |
| WO | 01/04333 | 1/2001 |
| WO | 01/83794 | 11/2001 |
| WO | 2009/000891 | 12/2008 |

OTHER PUBLICATIONS

Garcia-Sastre "Negative-strand RNA viruses: applications to biotechnology" TIBTECH May 1998 (vol. 16):230-235.*
Rota et al. et al. "Characterization of a Novel Coronavirus Associated with Severe Acute Respiratory Syndrome" Science 300:1394-1399, 2003.*
Ozawa et al. (Journal of Virology. 2007; 81 (17): 9556-9559).*
Horimoto et al. (Journal of Virology. 1994; 68 (5): 3120-3128).*
White et al. (Journal of Cell Biology. 1987; 105 (6, Pt. 2): 2887-2896).*
Shibata et al. (Journal of Virology. 1993; 67 (6): 3264-3273).*
Pleschka et al. (Journal of General Virology. 1995; 76: 2529-2537).*
Talon et al. (PNAS. 2000; 97 (8): 4309-4314).*
Ternovoi et al. (Journal of Virology. 2005; 79 (2): 1308-1311).*
Bentin et al., 1996, Biochemistry, 35:8863-8869.
Boyd M.R. and Beeson M.F., J. Antimicrobial Chemotherapy, 1975, 1 (suppl 4):43-47.
Couch 1993, Ann. NY. Acad. Sci 685:803-12.
Demidov et al., Biochem.Pharm., 1994, 48:1310-1313.
Demidov et al., Proc.Natl.Acad.Sci., 1995, 92:2637-2641.
Egholm et al., 1995, Nucleic Acids Res., 23:217-222.
Egorov et al. 1998 J. Virol. Aug. 1998; 72(8):6437-41.
Egorov et al., Vopr. Virusol., 1994, 39:201-205.
Gao et al. J.Virol., 2008, pp. 6419-6426.
Hoffmann E. et al., Virology, 2000, 267:310-317.
Hoffmann et al., Arch Virol., 2001, 146:2275-89.
Hoffmann et al., Proc.Natl.Acad.Sci., 2002, 99:11411-11416.
Hoffmann et al., Vaccine 2002, 20:3165-3170.
Lu et al. J. Virol., 1999, 73:5903-5911.
Luytjes et al., 1989, Cell, 59:1107-1113.
Neumann et al., 1994, Virology, 202:477-479.
Nielsen et al., Science, 1991, 254:1497-1500.
Ozawa M. et al., J.Virol, 2007, 81:9556-9559.
Pleschka et al., 1996, J. Virol., 70:4188-4192.
Williams et al., 1988, Ann. Intern. Med. 108:616.
International Search Report and Written Opinion, International Application No. PCT/EP2009/066358, Jan. 22, 2010.
Diaz, et al., "Clathrin adaptor AP1B controls adenovirus infectivity of epithelial cells," PNAS, 106(27):11143-11148 (Jul. 7, 2009).
Prevec, et al., "Use of Human Adenovirus-based Vectors for Antigen Expression in Animals," J. gen. Virol., 70:429-434 (1989).

* cited by examiner

*Primary Examiner* — Shanon A Foley
(74) *Attorney, Agent, or Firm* — Michael Fedrick; Loza & Loza, LLP

(57) ABSTRACT

The present invention provides a method for generating negative-strand, segmented RNA viruses using linear expression constructs in the presence of helper virus.

**19 Claims, 1 Dr

F4: bidirectional linear expression construct

SEQUENCE LISTING

<160> NUMBER OF SEQ ID NOS: 9

<210> SEQ ID NO 1
<211> LENGTH: 42
<212> TYPE: DNA
<213> ORGANISM: Influenza A virus

<400> SEQUENCE: 1
cgaagttggg ggggagcaaa agcaggggat aattctatta ac        42

<210> SEQ ID NO 2
<211> LENGTH: 44
<212> TYPE: DNA
<213> ORGANISM: Influenza A virus

<400> SEQUENCE: 2
gccgccgggt tattagtaga aacaagggtg tttttaatta atgc        44

<210> SEQ ID NO 3
<211> LENGTH: 32
<212> TYPE: DNA
<213> ORGANISM: Influenza A virus

<400> SEQUENCE: 3
cctgcttttg ctccccccca acttcggagg tc        32

<210> SEQ ID NO 4
<211> LENGTH: 34
<212> TYPE: DNA
<213> ORGANISM: artificial sequence
<220> FEATURE:
<223> OTHER INFORMATION: plasmid sequence

<400> SEQUENCE: 4
ggggtatcag ggttattgtc tcatgagcgg atac        34

<210> SEQ ID NO 5
<211> LENGTH: 36
<212> TYPE: DNA
<213> ORGANISM: Influenza A virus

<400> SEQUENCE: 5
ccttgtttct actaataacc cggcggccca aaatgc        36

<210> SEQ ID NO 6
<211> LENGTH: 32
<212> TYPE: DNA
<213> ORGANISM: artificial sequence
<220> FEATURE:
<223> OTHER INFORMATION: plasmid sequence

<400> SEQUENCE: 6
ccccttggcc gattcattaa tgcagctggt tc        32

<210> SEQ ID NO 7
<211> LENGTH: 11
<212> TYPE: PRT
<213> ORGANISM: artificial
<220> FEATURE:
<223> OTHER INFORMATION: modified HA cleavage site of influenza A virus

<400> SEQUENCE: 7

Pro Ser Ile Gln Pro Ile Gly Leu Phe Gly Ala
1               5                   10

<210> SEQ ID NO 8
<211> LENGTH: 1775
<212> TYPE: DNA
<213> ORGANISM: Influenza A virus

<400> SEQUENCE: 8

| | | | | | |
|---|---|---|---|---|---|
| agcaaaagca | ggggaaaata | aaacaacca | aatgaaagc | aaaactactg | gtcctgttat | 60 |
| gtacatttac | agctacatat | gcagacacaa | tatgtatagg | ctaccatgcc | aacaactcaa | 120 |
| ccgacactgt | tgacacagta | cttgagaaga | atgtgacagt | gacacactct | gtcaacctac | 180 |
| ttgaggacag | tcacaatgga | aaactatgtc | tactaaaagg | aatagcccca | ctacaattgg | 240 |
| gtaattgcag | cgttgccgga | tggatcttag | gaaacccaga | atgcgaatta | ctgatttcca | 300 |
| aggaatcatg | gtcctacatt | gtagaaacac | caaatcctga | gaatggaaca | tgttacccag | 360 |
| ggtatttcgc | cgactatgag | gaactgaggg | agcaattgag | ttcagtatct | tcatttgaga | 420 |
| gattcgaaat | attccccaaa | gaaagctcat | ggcccaacca | caccgtaacc | ggagtatcag | 480 |
| catcatgctc | ccataatggg | aaaagcagtt | tttacagaaa | tttgctatgg | ctgacgggga | 540 |
| agaatggttt | gtacccaaac | ctgagcaagt | cctatgtaaa | caacaaagag | aaagaagtcc | 600 |
| ttgtactatg | gggtgttcat | cacccgccta | acataggga | ccaaagggcc | ctctatcata | 660 |
| cagaaaatgc | ttatgtctct | gtagtgtctt | cacattatag | cagaagattc | accccagaaa | 720 |
| tagccaaaag | acccaaagta | agagatcagg | aaggaagaat | caactactac | tggactctgc | 780 |
| tggaacctgg | ggatacaata | atatttgagg | caaatggaaa | tctaatagcg | ccatggtatg | 840 |
| cttttgcact | gagtagaggc | tttggatcag | gaatcatcac | ctcaaatgca | ccaatggatg | 900 |
| aatgtgatgc | gaagtgtcaa | acacctcagg | gagctataaa | cagcagtctt | cctttccaga | 960 |
| atgtacaccc | agtcacaata | ggagagtgtc | caaagtatgt | caggagtgca | aaattaagga | 1020 |
| tggttacagg | actaaggaac | atcccatcca | ttcaacccat | tggtttgttt | ggagccattg | 1080 |
| ccggtttcat | tgaagggggg | tggactggaa | tggtagatgg | gtggtatggt | tatcatcatc | 1140 |
| agaatgagca | aggatctggc | tatgctgcag | atcaaaaaag | tacacaaaat | gccattaacg | 1200 |
| ggattacaaa | caaggtgaat | tctgtaattg | agaaaatgaa | cactcaattc | acagctgtgg | 1260 |
| gcaaagaatt | caacaaattg | gaaagaagga | tggaaaactt | aaataaaaaa | gttgatgatg | 1320 |
| ggtttctaga | catttggaca | tataatgcag | aattgttggt | tctactggaa | aatgaaagga | 1380 |
| ctttggattt | ccatgacttc | aatgtgaaga | atctgtatga | gaaagtaaaa | agccaattaa | 1440 |
| agaataatgc | caaagaaata | ggaaacgggt | gttttgaatt | ctatcacaag | tgtaacaatg | 1500 |
| aatgcatgga | gagtgtgaaa | aatggaactt | atgactatcc | aaaatattcc | gaagaatcaa | 1560 |
| agttaaacag | ggagaaaatt | gatggagtga | aattggaatc | aatgggagtc | tatcagattc | 1620 |
| tggcgatcta | ctcaactgtc | gccagttccc | tggttctttt | ggtctccctg | ggggcaatca | 1680 |
| gcttctggat | gtgttccaat | gggtctttgc | agtgtagaat | atgcatctga | gaccagaatt | 1740 |
| tcagaaatat | aagaaaaaac | acccttgttt | ctact | | | 1775 |

<210> SEQ ID NO 9
<211> LENGTH: 33
<212> TYPE: DNA
<213> ORGANISM: Influenza A virus

<400> SEQUENCE: 9
ccatccattc aacccattgg tttgtttgga gcc        33

METHOD FOR GENERATION OF RNA VIRUS

CROSS-REFERENCE TO RELATED APPLICATIONS

Figure 1A:
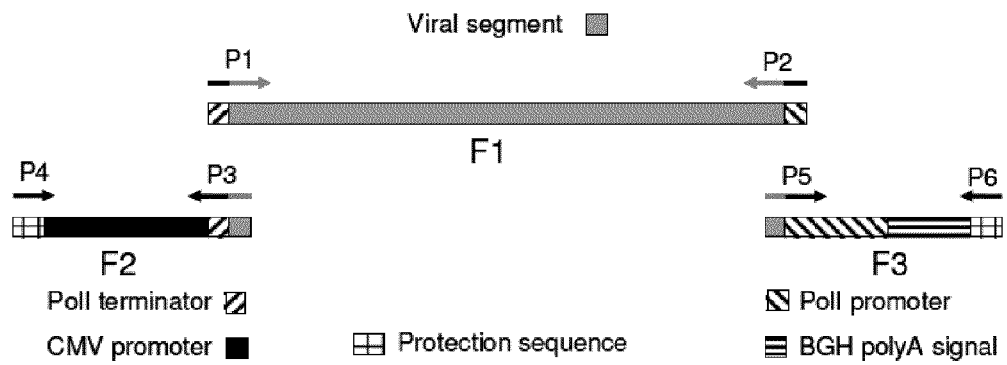

The present application claims the benefit of priority from U.S. Patent Application No. 61/119,618, filed on Dec. 3, 2008 and titled NOVEL METHOD FOR GENERATION OF RNA VIRUS. The disclosure of the foregoing application is incorporated herein by reference in its entirety.

SEQUENCE LISTING

The entire content of a Sequence Listing titled "Sequence_Listing.txt," created on Dec. 3, 2009 and having a size of 3.9 kilobytes, which is being submitted in electronic form herewith in connection with the present application, is incorporated by reference herein in its entirety.

FIELD OF THE INVENTION

The present invention provides a method for generating negative-stranded segmented RNA viruses using linear expression constructs in the presence of helper virus.

BACKGROUND OF THE INVENTION

Negative-strand RNA viruses are a group of animal viruses that comprise several important human pathogens, including influenza, measles, mumps, rabies, respiratory syncytial, Ebola and hantaviruses.

The genomes of these RNA viruses can be unimolecular or segmented, and are single stranded of (−) polarity. Two essential requirements are shared between these viruses: their genomic RNAs must be efficiently copied into viral RNA, a form which can be used for incorporation into progeny virus particles and transcribed into mRNA which is translated into viral proteins. Eukaryotic host cells typically do not contain the machinery for replicating RNA templates or for translating polypeptides from a negative-stranded RNA template. Therefore negative-strand RNA viruses encode and carry an RNA-dependent RNA polymerase to catalyze synthesis of new genomic RNA for assembly into progeny viruses and mRNAs for translation into viral proteins.

Genomic viral RNA must be packaged into viral particles in order for the virus to be transmitted. The processes by which progeny viral particles are assembled and the protein/protein interactions that occur during assembly are similar within the RNA viruses. The formation of virus particles ensures the efficient transmission of the RNA genome from one host cell to another within a single host or among different host organisms.

Virus families containing enveloped, single-stranded RNA with a negative-sense genome are classified into groups having non-segmented genomes (Paramyxoviridae, Rhabdoviridae, Filoviridae and Borna Disease Virus, Togaviridae) and those having segmented genomes (Orthomyxoviridae, Bunyaviridae and Arenaviridae). The Orthomyxoviridae family includes the viruses of influenza, types A, B and C viruses, as well as Thogoto and Dhori viruses and infectious salmon anemia virus.

Influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules of linear, negative polarity, single-stranded RNAs which encode eleven polypeptides (ten in some influenza A strains), including: the RNA-dependent RNA polymerase proteins (PB2, PB1 and PA) and nucleoprotein (NP) which form the nucleocapsid; the matrix membrane proteins (M1, M2); two surface glycoproteins which project from the lipid-containing envelope: hemagglutinin (HA) and neuraminidase (NA); the nonstructural protein (NS1) and nuclear export protein (NEP). Most influenza A strains also encode an eleventh protein (PB1-F2) believed to have proapoptotic properties.

Transcription and replication of the viral genome takes place in the nucleus and assembly occurs via budding on the plasma membrane. The viruses can reassort genes during mixed infections. Influenza virus adsorbs via HA to sialyloligo-saccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In other words, the eight viral RNA segments code for eleven proteins: nine structural and 2 non-structural (NS1 and the recently identified PB1-F2) proteins.

The generation of modern vaccines for influenza viruses, especially for highly pathogenic avian influenza viruses, relies on the use of reverse genetics, which allows the production of influenza viruses from DNA. The first reverse genetic systems for construction of negative-strand RNA influenza viruses involved the transfection of a single viral gene mixed with in-vitro reconstituted ribonucleoprotein (RNP) complexes and subsequent infection with an influenza helper virus. RNP complexes were made by incubating synthetic RNA transcripts with purified NP and polymerase proteins (PB1, PB2 and PA) from influenza viruses, and a helper virus was used as an intracellular source of viral proteins and of the other vRNAs (Luytjes et al., 1989, Cell, 59, 1107-1113).

Neumann et al. (1994, Virology, 202, 477-479) achieved RNP formation of viral model RNAs in influenza-infected cells after expression of RNA from a murine RNA polymerase I promoter-responsive plasmid. Pleschka et al. (1996, J. Virol., 4188-4192) described a method wherein RNP complexes were reconstituted from plasmid-based expression vectors. Expression of a viral RNA-like transcript was achieved from a plasmid containing a truncated human polymerase I (polI) promoter and a ribozyme sequence that generated a 3' end by autocatalytic cleavage. The polI-driven plasmid was cotransfected into human 293 cells with polII-responsive plasmids that expressed the viral PB1, PB2, PA and NP proteins. Transfection efficiency was very low, however, with approximately 10 transfectant virus particles per transfection. Additionally, this plasmid-based strategy was dependent on the aid of a helper virus.

In WO 01/04333, segmented negative-strand RNA viruses were constructed using a set of 12 expression plasmids for expressing genomic vRNA segments and RNP proteins. The vectors described in WO 01/04333 were based on well known pUC19 or pUC18 plasmids. According to the description, this system requires a set of 8 plasmids expressing all 8 segments of influenza virus together with an additional set of 4 plasmids expressing nucleoprotein and subunits of RNA-dependent RNA polymerase (PB1, PB2, PA and NP).

WO 00/60050 covers a set of at least two vectors comprising a promoter operably linked to an influenza virus segment cDNA (PA, PB1, PB2, HA, NP, NA, M) and linked to a transcription termination sequence, and at least two vectors comprising a promoter operably linked to an influenza virus segment DNA (PA, PB1, PB2, NP). This system attempted to overcome the difficulties in using of a large number of different vectors by using plasmids with eight RNA polymerase I transcription cassettes for viral RNA synthesis combined on one plasmid.

WO 01/83794 discloses circular expression plasmids comprising an RNA polymerase I (polI) promoter and a polI termination signal, inserted between a RNA polymerase II (polII) promoter and a polyadenylation signal. The term vector according to this application is described as a plasmid which generally is a self-contained molecule of double-stranded DNA that can accept additional foreign DNA and which can be readily introduced into a suitable host cell.

WO 2009/00891 describes a linear expression construct and its use for expression of influenza virus gene segments.

Ozawa M. et al (J. Virol, 2007, vol. 81, pp. 9556-9559) describes a reverse genetics system for the generation of influenza A virus using adenovirus vectors. Hoffmann E. et al (Virology, 2000, 267, pp. 310-317) disclose a system for creating influenza virus by generating viral RNA and mRNA from one template using a bidirectional transcription construct. The rescue of influenza B virus from eight plasmids was also disclosed in Hoffmann et al. (Proc. Natl. Acad. Sci., 2002, 99, pp. 11411-11416).

Epidemics and pandemics caused by viral diseases are still claiming human lives and are impacting the global economy. Influenza is responsible for millions of lost work days and visits to the doctor, hundreds of thousands of hospitalizations worldwide (Couch 1993, Ann. NY. Acad. Sci 685; 803,), tens of thousands of excess deaths (Collins & Lehmann 1953 Public Health Monographs 213:1; Glezen 1982 Am. J. Public Health 77:712) and billions of Euros in terms of health-care costs (Williams et al. 1988, Ann. Intern. Med. 108:616). When healthy adults get immunized, currently available vaccines prevent clinical disease in 70-90% of cases. This level is reduced to 30-70% in those over the age of 65 and drops still further in those over 65 living in nursing homes (Strategic Perspective 2001: The Antiviral Market. Datamonitor. p. 59). The virus's frequent antigenic changes further contribute to a large death toll because not even annual vaccination can guarantee protection. Hence, the U.S. death toll rose from 16,363 people in 1976/77 to four times as many deaths in 1998/99 (Wall Street Journal, Flu-related deaths in US despite vaccine researches. Jan. 7, 2003).

Especially in case of the outbreak of pandemic viral diseases, it can be of utmost importance to provide vaccinations or treatments immediately after outbreak of the disease. In view of the urgent need for providing efficient protection and treatment of viral diseases there is a still high demand for the development of economic, fast and efficient expression systems for virus production which can overcome the disadvantages and difficulties of the present expression technologies and provide an alternative method for virus expression. The object is achieved by the provision of the embodiments of the present application.

BRIEF SUMMARY OF THE INVENTION

The present invention provides an alternative technology wherein linear expression constructs are used for expression of RNA viruses in the presence of a helper virus.

It has been surprisingly found that the use of at least one linear expression construct free of any amplification and/or selection sequences comprising an RNA polymerase I (polI) promoter and a polI termination signal, inserted between an RNA polymerase II (polII) promoter, and a polyadenylation signal comprising a HA or a NA gene segment which is inserted between the polI promoter and the polI termination signal, in the presence of a helper virus provides an efficient tool for fast rescue of viral particles. In contrast to the methods used by known technologies, no cloning steps in bacterial cells are needed and host cells need not be transfected with all segments of the viral genome. Specifically, transfection with only one or two segments, i.e. genes coding for the HA and/or NA protein, can be sufficient for expression of whole virus. Therefore, the time needed for transfection and expression of sufficient amounts of viral particles can be highly reduced.

For example, a linear expression construct as described in PCT/EP2008/058182, which is incorporated herein by reference, can be used for developing vaccines comprising RNA viruses, specifically influenza viruses either of wild type, mutant or reassortant strains, in the presence of helper virus. This provides a tool for fast generation of any virus vaccine needed in case of the occurrence of influenza epidemics or pandemics.

Further, the present invention provides an improved method for removal of helper virus and provides HA segments with modified cleavage sites for improved selection and purification purposes.

FIGURES

Figure 1B:
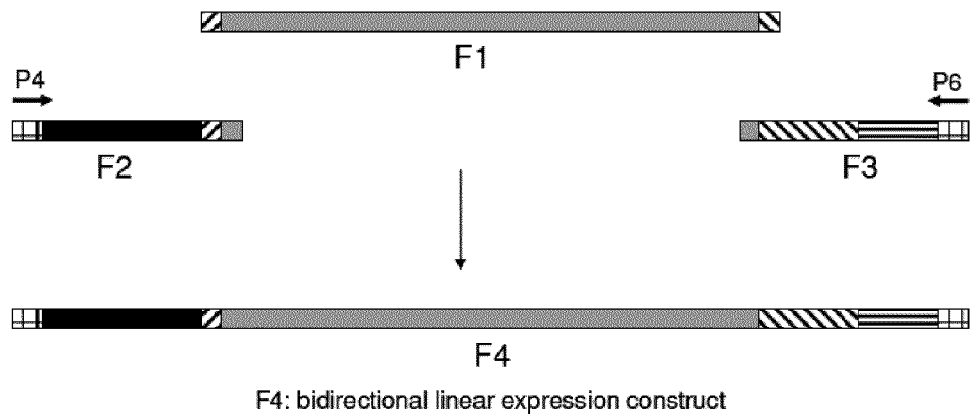

FIGS. 1a and 1b are schematic diagrams illustrating the generation of linear bidirectional expression constructs. FIG. 1a shows fragments F1, F2 and F3 being generated separately by PCR amplification. FIG. 1b shows fragment F4 being generated by overlapping PCR using the oligonucleotides P4 and P6.

DETAILED DESCRIPTION OF THE INVENTION

The present invention covers a method for production of negative stranded segmented RNA viruses comprising the steps of:

a) providing a linear expression construct free of any amplification and/or selection sequences, which construct comprises an RNA polymerase I (polI) promoter and a polI termination signal, both inserted between an RNA polymerase II (polII) promoter and a polyadenylation signal which construct further comprises a HA and/or a NA gene segment inserted between the polI promoter and the polI termination signal, b) transfecting a host cell with said linear expression construct, c) infecting said host cells with a helper virus having helper virus HA and/or NA proteins, d) cultivating said host cell to propagate virus particles, e) selecting virus particles, which contain:
   (i) the HA and/or NA proteins derived from the linear expression construct, but not
   (ii) the helper virus HA and NA proteins, or segments thereof, wherein said selection is based on phenotypic, genotypic or antigenic properties of the HA and/or NA proteins, and optionally wherein the absence of helper virus HA and NA proteins is determined by analysis of the nucleic acid or amino acid sequence.

More specifically the method for producing a negative-stranded, segmented RNA virus particle can comprise the steps of providing a linear expression construct free of amplification sequences, selection sequences, or both amplification sequences and selection sequences, wherein the construct comprises an RNA polymerase I (polI) promoter and a polI termination signal, the polI promoter and polI termination signal being inserted between an RNA polymerase II (polII) promoter and a polyadenylation signal, wherein the linear expression construct further comprises an HA gene segment, an NA gene segment, or both an HA gene segment and an NA gene segment inserted between the polI promoter and the polI termination signal; transfecting a host cell with the linear expression construct; infecting the host cell with a helper virus, wherein the helper virus comprises genomic RNA encoding HA protein, NA protein or both HA protein and NA protein; cultivating the host cell, thereby producing progeny virus particles, wherein at least some of the progeny virus particles comprise HA protein or NA protein derived from the linear expression construct; and selecting a candidate virus particle from among the progeny virus particles, wherein the candidate virus particle comprises:

i) HA protein derived from the linear expression construct and not HA protein derived from the helper virus, if the linear expression construct comprises an HA gene segment; and ii) NA protein derived from the linear expression construct and not NA protein derived from the helper virus, if the linear expression construct comprises an NA gene segment.

According to invention the host cell is transfected with at least one linear expression construct comprising an HA or NA gene segment. Preferably the host cell is transfected with at least two linear expression constructs wherein one linear construct comprises the HA gene segment and the second linear construct comprises the NA gene segment.

The step of selecting the candidate virus particle can further comprise analyzing amino acid sequences of the candidate virus particle in order to determine that the candidate virus particle does not comprise HA amino acid sequences or NA amino acid sequences of the helper virus or analyzing nucleic acid molecules of the candidate virus particle in order to determine that the candidate virus particle does not comprise HA nucleotide sequences or NA nucleotide sequences of the helper virus.

The "linear expression constructs" are defined according to the invention as being free of any amplification and/or selection sequences and comprising an RNA polymerase I (polI) promoter and a polI termination signal, inserted between an RNA polymerase II (polII) promoter and a polyadenylation signal and comprising a gene segment inserted between the polI promoter and the polI termination signal.

Preferably, the linear expression constructs do not contain any selection or amplification sequences that are needed for amplification of plasmids in bacterial cells. Neither on (origin of replication)-sequences nor antibiotics resistance genes or any other selection markers need to be contained. If needed, the linear expression construct can be circularized using short linker sequences.

According to a specific embodiment of the invention the linear expression construct can comprise molecules other than DNA molecules, such as additional protection sequences at the N- and/or C-terminus of the construct. For example, these protection sequences can be peptide nucleic acid sequences (PNAs) as described in WO 00/56914. These PNAs are nucleic acid analogs in which the entire deoxyribose-phosphate backbone has been exchanged with a chemically completely different, but structurally homologous, polyamide (peptide) backbone containing 2-aminoethyl glycine units. PNA "clamps" have also been shown to increase stability, wherein two identical PNA sequences are joined by a flexible hairpin linker containing three 8-amino-3,6-dioxaoctanoic acid units. When a PNA is mixed with a complementary homopurine or homopyrimidine DNA target sequence, a PNA-DNA-PNA triplex hybrid can form which is extremely stable (Bentin et al., 1996, Biochemistry, 35, 8863-8869, Egholm et al., 1995, Nucleic Acids Res., 23, 217-222, Nielsen et al., Science, 1991, 254, 1497-1500, Demidov et al., Proc. Natl. Acad. Sci., 1995, 92, 2637-2641). They have been shown to be resistant to nuclease and protease digestion (Demidov et al., Biochem. Pharm., 1994, 48, 1010-1013). The viral gene segment can be a cDNA copy or RT-PCR amplification product of said segment.

Specifically, the present invention provides a method for expression and production of an RNA virus comprising the steps of:

a) transfecting host cells with a linear expression construct comprising an HA gene segment and/or a linear expression construct comprising an NA gene segment and optionally linear expression constructs comprising further gene segments or at least part thereof selected from PB1, PB2, PA, NS, M, NP;

b) infecting said host cells with a helper virus;

c) cultivating the infected host cells to propagate viruses; and d) selecting virus particles containing at least HA and/or NA protein derived from said linear expression constructs.

Said selection can be performed based on genotypic, phenotypic or antigenic properties of the HA or NA proteins of non-helper virus origin. Any selection methods can be used as known to differentiate between proteins comprising different sequences, different phenotypic characteristics or different antigenic characteristics. Specifically, selection criteria can be used as described in the present invention. The HA and NA proteins from helper virus origin and non-helper virus origin vary in nucleotide and amino acid sequence, therefore sequences comparison methods as well known in the art can be used for identifying viruses comprising HA or NA sequences derived from the linear expression constructs. Nucleic acid molecules that are "derived from" an expression construct or a virus are those that comprise a nucleotide sequence of the expression construct or virus or a complementary sequence, and are generally produced as a result of the presence of the expression construct or virus in a cell culture or other medium for production of the molecules. Proteins that are "derived from" an expression construct or a virus are those which are translated from a nucleotide sequence of the expression construct or virus or a complementary sequence, and are generally produced as a result of the presence of the expression construct or virus in a cell culture or other medium for production of the proteins.

Additionally to the use of at least one linear expression construct, plasmids known in the art for performing reverse genetics techniques can be used for expression of viral proteins and/or further segments of the viral genome. These plasmids are for example described in Hoffmann et al. (Vaccine 2002, 20(25-26), 3165-3170, which is incorporated by reference). Specifically, these expression plasmids comprise the segments coding for PB1, PB2, PA, NS, NA, HA, M or NP or part thereof.

The term "HA protein" and "NA protein" are defined according to the present invention as the complete amino acid sequence of the HA or NA protein respectively or a part of said sequence wherein said part is sufficient to induce an immune response against said HA or NA protein similar or equal to the response produced by wild type HA or NA protein. Preferably, the HA or NA protein comprises at least 70% of the HA or NA amino acid sequence of the complete protein, preferably at least 90%, more preferably at least 95%. Functional equivalency in terms of immunogenicity can be tested for example in animal models as described in Lu et al. (J. Virol., 1999, 5903-5911) or Boyd M. R. and Beeson M. F. (J. Antimicrobial Chemotherapy, 1975, 43-47).

A helper virus is a virus used when producing copies of a helper dependent viral vector which does not have the ability to replicate on its own. The helper virus is used to coinfect cells alongside the viral vector and provides the necessary enzymes for replication of the genome of the viral vector.

The term "helper virus" is defined as any virus that comprises at least one gene segment identical to the virus to be produced and which can support the virus generation by providing at least one viral segment and/or at least one viral protein needed for producing complete virus particles.

The helper virus is generally added to the host cells in the present method after transfection with linear expression constructs, yet according to an alternative method, the helper virus can be added to the host cells for infection before the host cells are transfected by the expression construct comprising HA and/or NA gene segments.

The RNA viruses that can be expressed by said method can be any RNA virus comprising HA and/or NA gene segments or structures functionally equivalent to these structures. The term "functionally equivalent structures" means viral proteins that have receptor-binding and fusion activities.

The RNA viruses can be selected from the group consisting of influenza viruses, specifically influenza A, B or C viruses, coronavirus, Respiratory Syncytial virus, Newcastle disease virus.

The cells which can be used in the method according to the invention for cultivating the viruses can be any desired type of cells which can be cultured and which can be infected by enveloped viruses, specifically by influenza viruses. Specifically it can be BSC-1 cells, LLC-MK cells, CV-1 cells, CHO cells, COS cells, murine cells, human cells, HeLa cells, 293 cells, VERO cells, CEK (chicken embryo kidney) CEF (chicken embryo fibroblasts), MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0 cells, NS0, PerC6 (human retina cells).

According to the inventive method the host cells can be transfected by known methods, for example by electroporation.

The host cell culture can be cultured under standard conditions known in the art to replicate the viruses, in particular until a maximum cytopathic effect or a maximum amount of virus antigen can be detected. The harvesting can alternatively be at any time point during cultivation.

The pH for cultivation of the host cells, can be for example between 6.5 and 7.5. The pH for cultivation depends on the pH stability of the host cells used for cultivation. This can be determined by testing of the host cells' viability under different pH conditions.

It is well known in the art that the wild-type viruses used in preparation of the vaccine strains for annual vaccination against epidemic influenza are recommended annually by the World Health Organization (WHO). These strains may then used for the production of reassortant vaccine strains which generally combine the NA and/or HA genes of the wild-type viruses with the remaining gene segments derived from a donor virus (often referred to as a master donor virus or MDV) which will have certain desirable characteristics. For example, an MDV strain may be cold-adapted, and/or temperature sensitive, and/or attenuated, and/or have a high growth rate. According to the present invention the virus particles preferably comprise the HA and/or NA proteins of virus strains recommended for seasonal vaccination purposes or of virus strains which have shown to be highly immunogenic specifically in case of pandemic viruses.

The selection of viruses comprising said surface proteins can be based on phenotypic, genotypic or antigenic properties which differentiate said proteins from HA and NA proteins of helper virus origin.

Phenotypic properties of the HA and NA proteins of helper virus origin that differentiate said proteins from HA and NA proteins of non helper virus origin, like a selected virus comprises for example differences in the cleavage site for activation of HA or differs in the stability to low pH. The helper virus HA may contain a cleavage site that depends on proteolytic activation by a protease different from the protease activating the HA of the vaccine virus. The helper virus may also exhibit lower stability to low pH conditions than the vaccine virus.

Selection of viruses containing HA and NA of the vaccine virus may also be based on antigenic properties. By using a helper virus of a different subtype (e.g. H3N2) than the vaccine virus (e.g. H1N1) growth of the helper virus can be suppressed by an antiserum specific for helper virus subtype e.g. H3N2. Genotypic characteristics that may be exploited for selection include nucleic acid or amino acid sequence differences between the HA and/or NA segments of helper virus origin and HA and NA proteins of non helper virus origin. Methods are well known in the art to do sequence analysis.

Based on nucleotide sequence differences e.g. siRNAs or anti-sense oligonucleotides can be designed specifically for HA and/or NA of the helper virus. By transfection of these siRNAs or anti-sense oligonuclotides helper virus growth could be suppressed.

One option can be that virus particles comprising HA proteins of helper virus origin are separated from the candidate virus particles by treatment with a protease which does not cleave HA protein of helper virus origin but cleaves and thereby activates the HA protein of the reassortant virus. For example, the protease can be selected from the group consisting of trypsin, elastase, chymotrypsin, papain or thermolysin.

For example, the HA protein of the helper virus can be modified to be activated, e.g. cleavage, by a protease wherein said protease is not trypsin and whereas the HA protein of the final vaccine virus is cleaved by trypsin. Thereby a simple and applicable selection system is provided. This can be performed by modifying the cleavage site. The HA segment a virus strain useful as helper virus can be altered by mutagenesis, such as PCR-mutagenesis, to contain a cleavage site that is proteolytically activated by elastase instead of trypsin. For example, the amino acid sequence surrounding the cleavage site can be PSIQPI/GLFGA (the cleavage site is indicated by /).

To minimise unwanted reversion events codons are chosen in a way that at least two nucleotide changes per codon are preferably necessary to cause a reversion back to the original amino acid.

Alternatively the virus particles comprising HA and NA proteins of helper virus origin can be separated from the candidate virus particles comprising the NA or HA proteins expressed from the linear constructs by providing low pH conditions. Virus particles cultivated in cell culture for several passages, specifically in Vero cell culture, show reduced stability towards low pH due to modifications within the HA proteins compared to strains from clinical isolates comprising wild type HA and/or NA proteins. Thus treatment of the helper virus under low pH conditions, i.e. at a pH between 5.2 and 6.2 leads to reduced propagation rate of helper virus and therefore to a selection of candidate viral particles comprising unmodified HA and/or NA proteins.

As a further alternative embodiment of the invention virus particles comprising HA and/or NA proteins of helper virus origin are separated from the candidate virus particles by treatment with antiserum containing antibodies neutralising or binding to said HA and/or NA proteins of helper virus origin.

A combination of different methods to remove unwanted HA and NA proteins can also be performed according to the invention.

According to a specific embodiment of the invention, the helper virus particles can comprise NA protein with reduced activity compared to the NA protein of wild-type virus. The helper virus can in this embodiment lack a functional NA protein, i.e. an NA protein that enables the virus to be released from the host cell, or can lack the NA protein entirely.

According to a further alternative embodiment, the helper virus comprises the HEF protein of influenza C virus. Influenza C virus has only one major surface glycoprotein, HEF (hemagglutinin esterase fusion) which is functionally equivalent to HA protein. The HEF protein can be activated for example with trypsin or TPCK trypsin as described in Gao et al. (J. Virol., 2008, 6419-6426) which is incorporated herein by reference. Alternatively, modified influenza viruses comprising virus glycoprotein HEF that can be modified by introducing a foreign protease cleavage site, for example elastase cleavage site, are specifically claimed by the present invention.

As a further alternative embodiment of the invention, virus particles comprising HEF protein of helper virus origin are removed by treatment with antibodies neutralising or binding to said HEF protein.

As a further alternative, the helper virus can comprise the HA protein of a coronavirus. In case of production of influenza A virus, alternatively HA and/or NA proteins from influenza B origin can be used.

The virus for vaccine production as well as the helper virus can specifically be of influenza virus origin, more specifically it can be an attenuated influenza virus. According to a specific embodiment, the influenza virus is an attenuated influenza virus. Specifically the influenza virus comprises deletions or modifications within the pathogenicity factors inhibiting innate immune response of host cells. The attenuation can exemplarily be derived from cold-adapted virus strains or due to a deletion or modification within the NS1 gene (ΔNS1 virus) as described in WO99/64571 and WO99/64068 which are incorporated herein in total by reference. "Modification" refers to a substitution or deletion of one or more nucleic acids as compared to a wild-type NS1 sequence. Modification within the NS gene can lead to virus particles that are growth deficient in interferon competent cells. Growth deficient means that these viruses are replication deficient as they undergo abortive replication in the respiratory tract of hosts, and viral shedding thus is not observed in host animals which have been exposed to such viruses. Alternatively, the viruses can comprise deletion or modification of the PB1-F2 gene.

The method according to the invention can be specifically used for producing an influenza virus comprising a deletion of functional NS1 protein.

According to the invention the helper virus can contain at least 4, preferably at least 5, preferably 6 segments identical to the virus to be produced. Specifically, these segments are PB1, PB2, PA, NP, M, NS. Helper virus can be produced by known reverse genetics technologies or by alternative technologies like virus reassortment.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

A method for producing helper virus comprising NS1 deletions was described by Egorov et al. (1998 J. Virol. 1998 August; 72(8):6437-41; Egorov et al., Vopr. Virusol., 39:201-205). Thereby an H1 influenza A virus was used as basic virus comprising a temperature sensitive mutation within the NS gene that is further modified to result in completely deleted NS gene that can only grow in interferon deficient cells.

The present invention also covers a HA polypeptide comprising the sequence of PSIQPIGLFGA (SEQ ID. No. 7).

HA nucleotide sequence comprising following sequence or part thereof is also covered by the present invention:

```
                                              (SEQ ID No. 8)
AGCAAAAGCAGGGGAAAATAAAAACAACCAAAATGAAAGCAAAACTACTG

GTCCTGTTATGTACATTTACAGCTACATATGCAGACACAATATGTATAGG

CTACCATGCCAACAACTCAACCGACACTGTTGACACAGTACTTGAGAAGA

ATGTGACAGTGACACACTCTGTCAACCTACTTGAGGACAGTCACAATGGA

AAACTATGTCTACTAAAAGGAATAGCCCCACTACAATTGGGTAATTGCAG

CGTTGCCGGATGGATCTTAGGAAACCCAGAATGCGAATTACTGATTTCCA

AGGAATCATGGTCCTACATTGTAGAAACACCAAATCCTGAGAATGGAACA

TGTTACCCAGGGTATTTCGCCGACTATGAGGAACTGAGGGAGCAATTGAG

TTCAGTATCTTCATTTGAGAGATTCGAAATATTCCCCAAAGAAAGCTCAT

GGCCCAACCACACCGTAACCGGAGTATCAGCATCATGCTCCCATAATGGG

AAAAGCAGTTTTTACAGAAATTTGCTATGGCTGACGGGGAAGAATGGTTT

GTACCCAAACCTGAGCAAGTCCTATGTAAACAACAAAGAGAAAGAAGTCC

TTGTACTATGGGGTGTTCATCACCCGCCTAACATAGGGAACCAAAGGGCC

CTCTATCATACAGAAAATGCTTATGTCTCTGTAGTGTCTTCACATTATAG

CAGAAGATTCACCCCAGAAATAGCCAAAAGACCCAAAGTAAGAGATCAGG

AAGGAAGAATCAACTACTACTGGACTCTGCTGGAACCTGGGGATACAATA

ATATTTGAGGCAAATGGAAATCTAATAGCGCCATGGTATGCTTTTGCACT

GAGTAGAGGCTTTGGATCAGGAATCATCACCTCAAATGCACCAATGGATG

AATGTGATGCGAAGTGTCAAACACCTCAGGGAGCTATAAACAGCAGTCTT

CCTTTCCAGAATGTACACCCAGTCACAATAGGAGAGTGTCCAAAGTATGT
```

-continued

```
CAGGAGTGCAAAATTAAGGATGGTTACAGGACTAAGGAACATCCCATCCA

TTCAACCCATTGGTTTGTTTGGAGCCATTGCCGGTTTCATTGAAGGGGGG

TGGACTGGAATGGTAGATGGGTGGTATGGTTATCATCATCAGAATGAGCA

AGGATCTGGCTATGCTGCAGATCAAAAAGTACACAAAATGCCATTAACG

GGATTACAAACAAGGTGAATTCTGTAATTGAGAAAATGAACACTCAATTC

ACAGCTGTGGGCAAAGAATTCAACAAATTGGAAAGAAGGATGGAAAACTT

AAATAAAAAAGTTGATGATGGGTTTCTAGACATTTGGACATATAATGCAG

AATTGTTGGTTCTACTGGAAAATGAAAGGACTTTGGATTTCCATGACTTC

AATGTGAAGAATCTGTATGAGAAAGTAAAAAGCCAATTAAAGAATAATGC

CAAAGAAATAGGAAACGGGTGTTTTGAATTCTATCACAAGTGTAACAATG

AATGCATGGAGAGTGTGAAAAATGGAACTTATGACTATCCAAAATATTCC

GAAGAATCAAAGTTAAACAGGGAGAAAATTGATGGAGTGAAATTGGAATC

AATGGGAGTCTATCAGATTCTGGCGATCTACTCAACTGTCGCCAGTTCCC

TGGTTCTTTTGGTCTCCCTGGGGGCAATCAGCTTCTGGATGTGTTCCAAT

GGGTCTTTGCAGTGTAGAATATGCATCTGAGACCAGAATTTCAGAAATAT

AAGAAAAAACACCCTTGTTTCTACT
```

In particular, an HA nucleotide comprising the following sequence is included in the present invention: 5'-CCATCCATTCAACCCATTGGTTTGTTTGGAGCC-3' (SEQ ID. 9)

EXAMPLES

Example 1

Generation of a Linear H3N2 HA Expression Construct

The HA segment of a Vero cell culture-derived influenza A H3N2 virus was PCR amplified using the oligonucleotides P1 and P2 (F1 in FIG. 1a). Subsequently, two DNA fragments (F2 and F3 in FIG. 1) derived from pHW2000 (Hoffmann et al. 2000, Proc Natl Acad Sci USA. 97:6108-13) were fused to the HA PCR product by means of overlapping PCR (see FIG. 1b). The first DNA fragment (F2) comprises the CMV promoter and the PolI terminator, the second one (F3) comprises the human PolI promoter and the BGH polyA signal. To facilitate generation of the overlapping PCR products, oligonucleotides used for HA amplification were extended on their 5' ends in that P1 contains a sequence complementary to the PolI terminator and P2 contains a sequence complementary to the PolI promoter (see FIG. 1a). Similarly, the primers P3 and P5 used for generation of the fragments F1 and F2 were extended on their 5' termini to contain sequences complementary to the 5' and 3' end of the HA (see FIG. 1a).

Fragments F2 and F3 contain protection sequences derived from sequence described in the pHW2000 backbone. These sequences are not directly involved in transcription of mRNA and vRNA but reduce degradation of the bidirectional expression cassette by exonucleases.

Viral RNA was extracted from a Vero cell culture-derived influenza A H3N2 virus using a Qiagen ViralAmp kit and reverse transcribed using the Uni12 oligonucleotide as described previously (Hoffmann et al. 2001, Arch Virol. 146: 2275-89). The HA segment was amplified with the oligonucleotides shown in the table 1 using a mixture of Pfu Turbo DNA polymerase and Taq DNA polymerase:

TABLE 1

| P1 | 5'-CGAAGTTGGGGGG*AGCAAAAGCAGGGGATAATTCTATTAAC*-3'<br>(SEQ ID No. 1) |
|---|---|
| P2 | 5'-GCCGCCGGGTTAT*TAGTAGAAACAAGGGTGTTTTAATTAATGC*-3'<br>(SEQ ID No. 2) |

Nucleotides corresponding to the H3 sequence are shown in italic bold letters, nucleotides homologous to the PolI terminator (P1) and the PolI promoter (P2) are shown in standard capital letters.

The HA F4 PCR product was purified using a Qiaquick PCR Purification kit (Qiagen). PCR fragments F2 and F3 were amplified from pHW2000 plasmid DNA with the primer pairs P3+P4 and P5+P6 (see table 2 and FIG. 1a), respectively using a mixture of Pfu Turbo DNA polymerase and Taq DNA polymerase. PCR products F2 and F3 were purified using a Qiaquick PCR Purification kit (Qiagen)

TABLE 2

| P3 | 5'-*CCTGCTTTTGCT*CCCCCCCAACTTCGGAGGTC-3'<br>(SEQ ID No. 3) |
|---|---|
| P4 | 5'-GGGGTATCAGGGTTATTGTCTCATGAGCGGATAC-3'<br>(SEQ ID No. 4) |
| P5 | 5'-*CCTTGTTTCTACT*AATAACCCGGCGGCCCAAAATGC-3'<br>(SEQ ID No. 5) |
| P6 | 5'-CCCCTTGGCCGATTCATTAATGCAGCTGGTTC3'<br>(SEQ ID No. 6) |

For P3 and P5 nucleotides corresponding to the H3 sequence are shown in italic bold letters, nucleotides complementary to pHW2000 are shown in standard capital letters.

For P4 and P6 all nucleotides except the four nucleotides at the 5' ends correspond to pHW2000.

For generation of the full length PCR product (F4) containing the HA, the CMV promoter, the PolI terminator, the PolI promoter and the BGH polyA signal, fragments F1, F2 and F3 were combined and amplified by overlapping PCR with the primers P4 and P6 using a mixture of Pfu Turbo DNA polymerase and Taq DNA polymerase.

Figure 1B:

FIG. 1 shows a schematic diagram of the generation of linear bidirectional expression constructs. FIG. 1a) schematically discloses Fragments F1, F2 and F3 generated separately by PCR amplification.

Fragment F1 contains the respective viral segment and contains extensions complementary to the PolI promoter and PolI terminator. Fragment F2 contains the CMV promoter and the PolI terminator as well as an extension complementary to the respective viral segment. Fragment F3 contains the PolI promoter and the BGH poly adenylation signal as well as an extension complementary to the respective viral segment. Oligonucleotides P1 and P2 used for PCR amplification of F1 fragments are complementary to the respective viral segment. P1 contains a 5' extension complementary to the PolI terminator, P2 contains a 5'extension complementary to the PolI promoter.

Oligonucleotides P3 and P4 are used for PCR amplification of F2 fragments with P3 containing a 5'extension complementary to the respective viral segment.

Oligonucleotides P5 and P6 are used for PCR amplification of F3 fragment with P5 containing a 5'extension complementary to the respective viral segment.

Protection sequences are derived from the pHW2000 backbone and do not contain sequences directly involved in mRNA or vRNA transcription.

Example 2

Generation of an Elastase-Dependent Helper Virus

The HA segment of a influenza A/New Caledonia/20/99-like (H1N1) strain is altered by PCR-mutagenesis to contain a cleavage site that is proteolytically activated by elastase instead of trypsin. The amino acid sequence surrounding the cleavage site is changed from PSIQSR/GLFGA to PSIQPI/GLFGA (the cleavage site is indicated by /). Analogous to example 1, 10-20 µg linear bidirectional expression construct F4 are generated by PCR and purified using a Qiaquick kit (Qiagen) and subsequently via a Qiagen Endofree Plasmid kit.

Vero cells are maintained in DMEM/F12 medium containing 10% foetal calf serum and 1% Glutamax-I supplement at 37° C. and 5% CO2.

For virus generation the modified F4 HA DNA fragment is used alone or together with four protein expression plasmids coding for PB1, PB2, PA and NP for transfection of Vero cells. 24 h after transfection cells are infected at an MOI of 0.001 to 1 with an influenza A IVR-116 strain that does not express a functional NS1 (IVR-116-deINS1). Following infection, to support virus replication, Vero cells are cultured in serum-free medium (Opti-Pro; Invitrogen) in the presence of 5 µg/ml elastase. As soon as 50-100% CPE is observed the rescued elastase-dependent IVR-116-deINS1 virus (IVR-116-deINS1-EL) is frozen or plaque-purified on Vero cells.

Example 3

Generation of an Influenza A H3N2 Reassortant Virus by Using an Elastase-Dependent H1N1 Helper Virus Linear bidirectional expression constructs (F4) for the HA and NA segments of a A/Brisbane/10/2007 (H3N2)-like virus are generated by PCR as described in example 1. Following purification as described in example 2 the HA and NA F4 PCR products are used alone or together with four protein expression plasmids coding for PB1, PB2, PA and NP for transfection of Vero cells. 24 h after transfection cells are infected at an MOI of 0.001 to 1 with influenza A IVR-116-deINS1-EL virus (helper virus). Following infection cells are incubated in serum-free medium (Opti-Pro; Invitrogen) in the presence of 5 µg/ml trypsin. As soon as 10-100% CPE is observed virus is harvested. A selective passage is performed by treating the viral harvest for 24 h at 4° C. with appropriate concentrations (e.g. 10% v/v) of antisera (pretreated with neuraminidase from *Vibrio cholerae*) or of a purified IgG preparation specific for A/New Caledonia/20/99 HA and NA to neutralise helper virus. Vero cells are then incubated for 30 min at RT with pretreated virus, washed with PBS and subsequently incubated at 37° C. in serum-free medium containing 5 µg/ml trypsin. Optionally, purified IgG specific for A/New Caledonia/20/99 HA and NA may be added to the culture medium. As soon as 10-100% CPE is observed virus is harvested and a second selective passage is performed. Upon development of CPE virus is frozen or plaque-purified.

Example 4

Generation of an Influenza A H3N2 Reassortant Virus by Using an Elastase-dependent H1N1 Helper Virus in Combination with Low pH Treatment Linear bidirectional expression constructs (F4) for the HA and NA segments of a A/Brisbane/10/2007 (H3N2)-like virus are generated by PCR as described in example 1. Following purification as described in example 2 the HA and NA F4 PCR products are used alone or together with four protein expression plasmids coding for PB1, PB2, PA and NP for transfection of Vero cells. 24 h after transfection cells are infected at an MOI of 0.001 to 1 with influenza A IVR-116-deINS1-EL virus (helper virus). Following infection cells are incubated in serum-free medium (Opti-Pro; Invitrogen) in the presence of 5 µg/ml trypsin. As soon as 10-100% CPE is observed virus is harvested. Viral harvest is then diluted 1:1 with buffer containing 150 mM NaCl, and 50 mM MES pH 5.4-6.2 and incubated for 30 min at 37° C. to preferentially inactivate helper virus HA. Following pH neutralisation a selective passage can then performed by incubating the viral harvest for 24 h at 4° C. with appropriate concentrations (e.g. 10% v/v) of antisera (pretreated with neuraminidase from *Vibrio cholerae*) or of a purified IgG preparation specific for A/New Caledonia/20/99 HA and NA to neutralise helper virus. Vero cells are then incubated for 30 min at RT with pretreated virus, washed with PBS and subsequently incubated at 37° C. in serum-free medium containing 5 µg/ml trypsin. Optionally, purified IgG specific for A/New Caledonia/20/99 HA and NA may be added to the culture medium. As soon as 10-100% CPE is observed virus is harvested and a second selective passage is performed. Upon development of CPE virus is frozen or plaque-purified.

Example 5

Generation of an Influenza A H1N1 Reassortant Virus by Using an Elastase-Dependent H3N2 Helper Virus Linear bidirectional expression constructs (F4) for the HA and NA segments of a A/New Caledonia/20/99 (H1N1)-like virus are generated by PCR as described in example 1. Following purification as described in example 2 the HA and NA F4 PCR products are used alone or together with four protein expression plasmids coding for PB1, PB2, PA and NP for transfection of Vero cells. 24 h after transfection cells are infected at an MOI of 0.001 to 1 with an elastase-dependent influenza A/Wisconsin/67/05 (H3N2)-like virus (helper virus). Following infection cells are incubated in serum-free medium (Opti-Pro; Invitrogen) in the presence of 5 µg/ml trypsin. As soon as 10-100% CPE is observed virus is harvested. A selective passage is performed by treating the viral harvest for 24 h at 4° C. with appropriate concentrations (e.g. 10% v/v) of antisera (pretreated with neuraminidase from *Vibrio cholerae*) or of a purified IgG preparation specific for A/Wisconsin/67/05 HA and NA to neutralise helper virus. Vero cells are then incubated for 30 min at RT with pretreated virus, washed with PBS and subsequently incubated at 37° C. in serum-free medium containing 5 µg/ml trypsin. Optionally, purified IgG specific for A/Wisconsin/67/05 HA and NA may be added to the culture medium. As soon as 10-100% CPE is observed virus is harvested and a second selective passage is performed. Upon development of CPE virus is frozen or plaque-purified.

The invention claimed is:

1. A method for producing an influenza virus particle, comprising the steps of:
   a) providing a linear expression construct free of amplification sequences needed for amplification of plasmids in bacterial cells, selection markers, or both amplification sequences and selection markers, wherein the construct comprises an RNA polymerase I (polI) promoter and a polI termination signal, the polI promoter and polI termination signal being inserted between an RNA polymerase II (polII) promoter and a polyadenylation signal, wherein the linear expression construct further comprises a gene segment selected from the group consisting of an HA gene segment of an influenza virus, an NA gene segment of an influenza virus, or both an HA gene segment and an NA gene segment of an influenza virus, and wherein the gene segment is inserted between the polI promoter and the polI termination signal;
   b) transfecting a host cell with the linear expression construct;
   c) infecting the host cell with a helper virus, wherein the helper virus is an influenza virus, and wherein the helper virus comprises genomic RNA encoding a protein selected from the group consisting of HA protein of an influenza virus, NA protein of an influenza virus or both HA protein and NA protein of an influenza virus, the helper virus further comprising other viral segments needed to produce progeny virus particles;
   d) cultivating the host cell, thereby producing progeny virus particles, wherein at least some of the progeny virus particles comprise HA protein or NA protein derived from the linear expression construct; and
   e) selecting a candidate virus particle from among the progeny virus particles, wherein the candidate virus particle comprises:
      i) HA protein derived from the linear expression construct and not HA protein derived from the helper virus, if the linear expression construct comprises an HA gene segment; and
      ii) NA protein derived from the linear expression construct and not NA protein derived from the helper virus, if the linear expression construct comprises an NA gene segment.

2. A method according to claim 1, further comprising the step of transfecting the host cell with a linear expression construct that encodes a protein selected from the group consisting of PB1, PB2, PA, NS, M, and NP.

3. A method according to claim 1, wherein the step of selecting the candidate virus particle comprises analyzing amino acid sequences of the candidate virus particle in order to determine that the candidate virus particle does not comprise an HA amino acid sequence or NA amino acid sequence of the helper virus.

4. A method according to claim 1, wherein the step of selecting the candidate virus particle comprises analyzing nucleic acid molecules of the candidate virus particle in order to determine that the candidate virus particle does not comprise an HA nucleotide sequence or NA nucleotide sequence of the helper virus.

5. A method according to claim 1, wherein progeny virus particles comprising HA protein derived from the helper virus are separated from the candidate virus particle by treating the progeny virus particles with a protease, and wherein the protease does not cleave HA protein derived from the helper virus but cleaves the HA protein of the candidate virus particle.

6. A method according to claim 5, wherein the protease is selected from the group consisting of trypsin, elastase, chymotrypsin, and papain.

7. A method according to claim 1, wherein the helper virus comprises genomic RNA encoding HA protein and the HA protein can be cleaved by a protease, and wherein the protease is not trypsin.

8. A method according to claim 1, wherein progeny virus particles comprising HA protein or NA protein derived from the helper virus are separated from candidate virus particles under low pH conditions.

9. A method according to claim 1, wherein progeny virus particles comprising HA protein or NA protein derived from the helper virus are separated from the candidate virus particle by contacting the progeny virus particles with antibodies binding the HA protein or NA protein derived from the helper virus.

10. A method according to claim 1, wherein the helper virus comprises genomic RNA encoding NA protein with reduced activity compared to wild-type NA protein.

11. A method according to claim 1, wherein the helper virus lacks genomic RNA coding for NA protein or comprises genomic RNA coding for NA protein that does not enable the virus to be released from the host cell.

12. A method according to claim 1, wherein the helper virus comprises the HEF protein of influenza C virus.

13. A method according to claim 12, wherein the HEF protein of the helper virus is modified to be cleaved by a protease, and wherein the protease is not trypsin.

14. A method according to claim 1, wherein the candidate virus particle is an attenuated influenza virus particle.

15. A method according to claim 1, wherein the other viral segments needed to produce progeny virus particles comprise an NS1 gene, the NS1 gene having a deletion or modification compared to a wild-type NS1 gene.

16. A method according to claim 1, wherein the other viral segments needed to produce progeny virus particles comprise an NS1 gene, the NS1 gene having a deletion or modification compared to a wild-type NS1 gene and is growth deficient in interferon competent cells.

17. A method according to claim 1, wherein the helper virus contains at least 4 segments identical to the candidate virus.

18. A method according to claim 1, wherein the helper virus contains at least 5 segments identical to the candidate virus.

19. A method according to claim 1, wherein the helper virus contains at least 6 segments identical to the candidate virus.

* * * * *